United States Patent [19]

Unno et al.

[11] 4,144,354

[45] Mar. 13, 1979

[54] METHOD FOR PROMOTING SECRETION OF MILK OF LIVESTOCK

[75] Inventors: Naoyuki Unno, Tokyo; Mutsuyuki Yoshino; Minoru Murata, both of Chiba, all of Japan

[73] Assignee: Kyowa Hakko Kogyo Co., Ltd., Japan

[21] Appl. No.: 766,863

[22] Filed: Feb. 9, 1977

[30] Foreign Application Priority Data

Feb. 12, 1976 [JP] Japan .................................. 51-13172

[51] Int. Cl.$^2$ ........................ A23K 1/18; A61K 37/48
[52] U.S. Cl. ......................................... 426/2; 426/53; 424/94; 195/66 R
[58] Field of Search ................. 426/2, 53, 63; 424/94, 424/93; 195/66 R

[56] References Cited

U.S. PATENT DOCUMENTS

3,097,145   7/1963   Shimazono et al. ............... 195/66 R
3,694,316   9/1972   Kawai et al. ...................... 195/66 R

FOREIGN PATENT DOCUMENTS

211641   11/1957   Australia ...................................... 426/2

OTHER PUBLICATIONS

Chemical Abstract 85:3848y "Studies on the production of fermented feeds from agricultural waste products".

*Primary Examiner*—Raymond N. Jones
*Assistant Examiner*—Elizabeth A. Hatcher
*Attorney, Agent, or Firm*—Craig & Antonelli

[57] ABSTRACT

Enzyme composition having the activities of cellulase laminarinase, xylanase, dextranase, amilase, pectinase and protease which is obtained by culturing Basidiomycetes belonging to the genus Irpex is used for promoting secretion of milk of livestock and improving the quality of the milk.

5 Claims, No Drawings

METHOD FOR PROMOTING SECRETION OF MILK OF LIVESTOCK

BACKGROUND OF THE INVENTION

This invention relates to an enzyme composition for increasing secretion of milk of livestock and improving quality of the milk.

Nutritive value of milk of livestock, especially cows, is highly estimated, and the milk of cows is a livestock product widely utilized as raw materials for processed dairy products such as powdered milk, butter, cheese, etc., or as a beverage, and holds a very important position in the modern food life.

In the production of milk of livestock, various attempts have been so far made to increase the amount of secretion of milk and to improve the qualities of milk from the standpoints of genetics, livestock nutrition science and veterinary science. However, it is still a great task for livestock breeders and manufacturers of dairy products to further increase the amount of secretion of milk of livestock and to improve the quality of the milk.

As a result of studies on a process for improving the production of milk of livestock, the present inventors have found that by giving livestock an enzyme composition obtained by culturing Basidiomycetes belonging to the genus Irpex, the secretion of milk of livestock is promoted and the quality of the milk is improved, and thus have completed the present invention.

It is known that said enzyme composition has the activities of cellulase, laminarinase, xylanase, pectinase, dextranase, amylase and protease.

In the livestock industry, it is widely adopted to feed enzymes to single-stomach animals such as pigs, hens, horses, etc. to improve the feed efficiency, promote the digestion, etc. Also in the dairy farming, it is known to use enzymes in the production of dairy products. However, no attempt has so far been made to give enzymes to livestock to increase the amount of secretion of milk and to improve the quality of the milk as in the present invention. That is, such an attempt has been made for the first time by the present inventors.

SUMMARY OF THE INVENTION

According to the present invention, the amount of secretion of milk, milk fat ratio, non-fat solid content, etc. can be increased by administering to livestock the enzyme composition having the activities of cellulase, laminarinase, xylanase, pectinase, dextranase, amylase and protease which is obtained by culturing Basidiomycetes belonging to the genus Irpex.

DETAILED EXPLANATION OF THE INVENTION

In the present invention, a great effect can be expected by administering an enzyme composition to livestock for milking, such as cows, goats, sheep, etc.

The enzyme composition used in the present invention can be obtained by culturing strains belonging to the genus Irpex in a solid medium or a liquid medium.

Examples of the preferred strains are *Irpex lacteus* FERM-P No. 1009, NRRL No. 11063 and *Irpex lacteus* ATCC 20123.

*Irpex lacteus* FERM-P No. 1009, NRRL No. 11063 has been deposited with the Fermentation Research Institute, Agency of Industrial Science and Technology at 1-8-5, Inage Higashi, Chiba-shi, Chiba-ken, Japan, and with the Northern Regional Research Laboratory, 1815 North University Street, Peoria, Ill., 61604, U.S.A. *Irpex lacteus* ATCC 20123 has been deposited with the American Type Culture Collection, Rockville, Md., U.S.A.

The microbiological properties of the strain belonging to these strains are described in "Genshoku Nippon Kinrui Zukan" (Colored Encyclopedia of Japanese Microorganisms) vol. 1, 1957 published by Hoiku-sha.

The method for culturing Basidiomycetes is disclosed, for example, in Journal of Fermentation Technology, Japan, vol. 50 691–697 (1972), and is obvious to those skilled in the art. The method is described below.

Either a synthetic culture medium or a natural nutrient medium may be used so long as it properly contains a main carbon source, a nitrogen source, inorganic compounds and other nutrients. As the carbon source, carbohydrates such as starch, dextrin, sucrose, lactose, maltose, blackstrap molasses, starch hydrolyzate, etc., and substances such as wood hydrolyzate, cellulose, sawdust, pulp chip, etc. may be used. These carbon sources may be used either singly or in mixture of two or more. As the nitrogen source, ammonium chloride, ammonium sulfate, ammonium nitrate, ammonium acetate, ammonium phosphate, etc., and natural substances containing nitrogen such as corn steep liquor, yeast extract, meat extract, peptone, fish meal, bouillon, casein hydrolyzate, soybean meal, wheat bran, yeast, fish solubles, rice bran extract, distillers soluble, etc. may be used. As inorganic compounds, magnesium sulfate, sodium phosphate, potassium dihydrogen phosphate, potassium monohydrogen phosphate, iron sulfate, manganese chloride, calcium chloride, sodium chloride, etc. may be used. Further, nutrients such as vitamins, growth-promoting substances, for example, biotin and amino acids such as glutamic acid or aspartic acid, and the like may be added to the medium as desired.

Culturing is carried out under aerobic conditions at a culturing temperature of preferably about 25° to 35° C. The pH of the medium during culturing should be kept within the range of from 2 to 7. Usually, culturing is conducted for 2–10 days.

The enzyme composition is generally prepared from an enzyme solution obtained by removing cells from a culture liquor according to conventional enzyme purification methods such as organic solvent precipitation, salting out, concentration under reduced pressure, adsorption and desorption by ion exchange.

However, the cells, culture filtrate, etc. after the culturing in said medium, can also be used as an enzyme source without further treatment.

The enzyme composition obtained according to the method described above has the following activity of the enzymes.

| Enzyme | Substrate | | Activity |
| --- | --- | --- | --- |
| Cellulase | Filter paper | u/g | 20,000 – 40,000 |
| Xylanase | Xylan | r/mg-hr | 1,600 – 3,400 |
| Dextranase | Dextrin | r/mg-hr | 10 – 120 |
| Laminarinase | Laminarin | r/mg-hr | 2,000 – 4,600 |
| Amylase | Starch | u/mg | 4 – 15 |
| Protease | Casein | u/mg | 2 – 20 |
| Pectinase | Pectin | %/0.3 mg | 26 – 81 | r: The amount of reduced sugar (as glucose) produced by 1 mg of the enzyme in hour.

The methods of the measurement of the enzyme activities are as follows:

I. Measurement of cellulase activity (Procedure)

Diluted enzyme solution *1

←— 2 pieces of filter paper *2

L-type test tube *3 shaking in Monod type incubator at 40° C. *4

Measurement of the time required for the complete disintegration of filter paper (min.) *5

---

*1 Diluted enzyme solution: An appropriate amount of the sample is dissolved in M/10 acetate buffer of pH 4.5 so that the average time of disintegration may be about 60 minutes. When an enzyme solution with concentration of 200 u/5 ml is used, filter paper will be disintegrated in 50 minutes. The buffer solution without enzyme is used as control.
*2 Toyo Roshi No. 51 Special (for measuring filter paper disintegrating activity of cellulase); 1 cm × 1 cm in size
*3 L-type test tube; inside diameter, 17 – 18 mm, vertical part, 75 – 76 mm in height; horizontal part, 150 mm in length.
*4 Monod-type incubator: 60 shaking/min; amplitude, 4 cm
*5 Average time of digestion: Five test tubes containing a sample are subjected to the test at the same time.

(Calculation)

The activity is indicated as a unit, 10,000 unit being defined as that amount of the enzyme which completely disintegrates the filter paper in one minute and the activity is calculated according to the following formula.

$$\text{Activity (u/g)} = \frac{25{,}000}{\text{Average time of disintegration (min)}} \times \frac{1{,}000}{\text{Amount of sample in 5 ml of diluted enzyme solution (mg)}}$$

The average time is calculated for the three disintegration times except maximum and minimum disintegration time.

To obtain the activity of a liquid, the number of units per ml instead of per g is calculated and the activity is represented by μ/ml.

II. Measurement of laminarinase activity 2.5% Laminarin solution in water: 1 ml ←— M/10 acetate buffer, pH 4.5, 3ml ←— Diluted enzyme solution 1 ml *1

Incubation at 40° C., 60 minutes

Stop the reaction by keeping in boiling water for 5 minutes

Determination of reducing sugar in reaction solution

---

*1 The enzume is dissolved in M/10 acetate buffer of pH 4.5

Buffer instead of diluted enzyme solution is used as the control.

(Calculation)

The activity of enzyme is represented by the amount(r) of reduced sugar produced by 1 mg of the enzyme in 60 minutes.

$$\frac{\text{Reduced sugar in reaction solution} - \text{Reduced surgar in control solution} - \text{Reduced sugar from enzyme in reaction solution}(r)}{\text{Amount of enzyme used (mg) · hour}}$$

III. Measurement of dextranase activity

The same procedure and calculation described in the measurement of laminarinase activity are repeated except using 2.5% dextrin solution in water as substrate.

IV. Measurement of xylanase activity

The same procedure and calculation described in the measurement of laminarinase activity are repeated except using 2.5% xylan solution in water as substrate.

V. Measurement of pectinase activity

Viscosity depression method (Procedure)

Ostwald'x viscometer

←— ,5 Acetate buffer, pH 4.5, 2 ml

←— 2 % pectin solution, 2 ml *1

Preheating, 40° C, 10 mins *2

←— Diluted enzyme solution 1 ml *3

Incubation, 40° C., 10 minutes, then measurement of viscosity (sec)

---

*1 : 2 % pectin solution in water
*2 : To measure viscosity, great care must be taken about preheating.
*3 : The enzyme is dissolved in M/10 acetate buffer of pH 4.5.

(Calculation)

The activity is represented by the percentage of viscosity depression per unit amount of the enzyme used.

$$\frac{V_o - V_t}{V_o - V_w} \times 100 \% \,/\, \text{Amount of enzyme used}$$

Vo: Time (second) required for flowing down of liquid which contains de-ionized water instead of enzyme solution.
Vt: Time required for flowing down of reacted solution 10 mins after the addition of enzyme solution
Vw: Time required for flowing down of de-ionized water.

VI. Measurement of amylase activity

The method of the measurement is described in "Method of Enzymatic Analysis" vol. 1 p 432 (1974) published by Academic Press, New York.

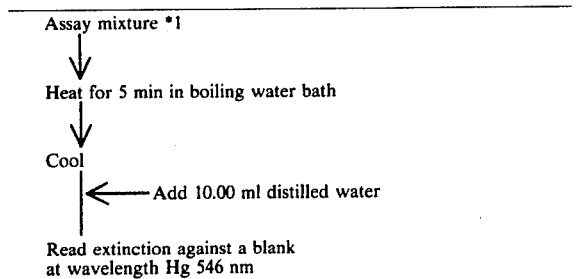

*1 0.50 ml Starch solution (10 mg starch/ml in 20 mM phosphate buffer, pH 7.0, 6 mM NaCl)
0.48 ml Distilled water
0.02 ml Enzyme soltuion in distilled water
1.00 ml Colour reagent (1 g 3,5-dinitrosalicyclic acid in 20 ml, 2N NaOH 30 g K-Na tartrate, distilled water to 100 ml)

VII. Measurement of protease activity

Protease activity is measured by Casein Folin method described in "Koso Kenkyu Method (enzyme research method)" vol. 2 pp 237–246 (1956) published in Japan.

Driselase (Trade mark, made by Kyowa Hakko Kogyo Co. Ltd.) that is enzyme composition obtained by culturing Basidiomycetes belonging to the species *Irpex lacteus* is on the market in Japan as feed additive enzyme and may be used as an enzyme source in the present invention.

According to the present invention, the enzyme composition may be administered as it is, but is usually administered in mixture with feed.

The effective amount of the enzyme composition to be administered is one or more units based on the cellulase activity per 1 g of the dry matter of feed. It is preferable to use 2–6 units of the enzyme composition based on the cellulase activity per 1 g of the dry matter of feed.

After two or three days from the starting of the administration, the amount of secretion of milk begins to increase. The high amount of secretion of milk is maintained during the administration of the enzyme composition and until after two or three days from the stop of the administration. Accordingly, the enzyme composition should be administered for at least three days running.

When the enzyme composition is administered to milch cows, the amount of secretion of milk, the non-fat solid content and the milk fat ratio are increased respectively by 8–12%, about 3% and about 5%.

The following experiments illustrate the effects of administration of the enzyme composition.

EXPERIMENT 1

The feed of which the composition was fixed (hereinafter referred to as fixed feed) was fed to 10 grown cows of Holstein variety in secretion of milk for 10 days as the preliminary period [5 kg of weeds, 3 kg of straws, 3 kg of hay cubes, 2 kg of beet pulp, 7 kg of bean and refuse, 5.5 kg pressed barley, 1 kg of wheat bran, and 1.5 kg of soybean meal were fed to one head per day (about 15 kg as the dry matter)]. The amount of milk, non-fat solid content, and milk fat ratio were measured during that period. For the following 30 days, 30 g of Driselase having a cellulase activity of 1,000 units/g per head per day was added to the fixed feed, and fed to the cows. Said Driselase has also the following enzyme activities: xylanase: 120 r/mg-hr, dextranase: 4 r/mg-hr, laminarinase: 100 r/mg-hr, amylase: 0.5 μ/mg, protease: 0.5 μ/mg and pectinase: 2.5%/0.3 mg. The amount of milk, non-fat solid content, and milk fat ratio were measured during that period. Then, only the fixed feed was fed to the cows as a trace test for a period of 20 days, and the amount of milk, non-fat solid content, and milk fat ratio were measured during that period. Averages of the measured values obtained during these three periods are given in Table 1.

Table I

| Period | Days | Cows Tested | Average amount of milk | Non-fat solid content | Milk fat ratio |
|---|---|---|---|---|---|
| Preliminary | 10 | 10 | 17.4 kg | 8.40 % | 3.20 % |
| Driselase administration | 30 | 9* | 19.3 kg | 8.60 % | 3.35 % |
| Trace | 20 | 8** | 17.7 kg | 8.45 % | 3.25 % |

*Average of 9 cows, because one cow was out of service.
**Average of 8 cows, because one cow had a doubt of disease (mastitis).

EXPERIMENT 2

Fifteen milch cows having a lower milk secretion ratio than the average were selected from the grown cows of Holstein variety raised in pasture and were tested in 3 groups each consisting of 5 head.

15 cows were divided into three groups A, B and C, each consisting of 5 head, and feed and enzyme-added feed were given to the cows as shown in Table 2.

Table 2

| Period \ Days | 1st to 10th day | 11th to 25th day | 26th to 40th day | 41st to 55th day | 56th to 70th day | 71st to 80th day |
|---|---|---|---|---|---|---|
| Enzyme addition | | A | A,B | B,C | C | |
| No enzyme addition | A,B,C | B,C | C | A | A,B | A,B,C |

As the feed containing no enzyme, 6.5 g of pressed barley, 1.6 kg of wheat bran; 3.9 kg of combined feed (Zenraku No. 2), 2.1 kg of hay cubes, and 5 kg of shredded rice straw (about 13 kg as the dry matter) was fed per head per day. As the feed containing the enzyme, the above feed further containing 30 g of the same Driselase as used in Experiment 1 was fed per head per day.

During the test, the cows were milked group by group, twice a day in the morning and the evening and an average amount of milk (kg) and an average milk fat content (%) per head were measured. The results are given in Table 3.

Table 3

| Period \ Days | 1st to 10th day | 11th to 25th day | 26th to 40th day | 41st to 55th day | 56th to 70th day | 71st to 80th day |
|---|---|---|---|---|---|---|
| Enzyme addition | | A 19.2* (3.15) | A 19.5 (3.17) B 19.3 (3.10) | B 19.6 (3.12) C 19.2 (3.14) | C 19.7 (3.17) | |
| | 17.3 | | | | | |

Table 3-continued

| Period | Days | 1st to 10th day | | 11th to 25th day | | 26th to 40th day | | 41st to 55th day | | 56th to 70th day | | 71st to 80th day |
| --- | --- | --- | --- | --- | --- | --- | --- | --- | --- | --- | --- | --- |
| No enzyme addition | A | (2.90) | B | 17.5 (2.90) | | | | | A | 17.4 (2.92) | A (2.92) | 17.4 |
| | B | 17.5 (2.90) | | | C | 17.4 (2.92) | A | 17.8 (2.96) | | | B | 17.6 (3.04) |
| | C | 17.4 (2.92) | C | 17.3 (2.91) | | | | | B | 17.8 (3.08) | C | 17.5 (3.02) |

*Figure in the upper row shows the amount of milk (kg) and figure in parentheses in the lower row shows the milk fat ratio(%).

The following is an example of the production of the enzyme composition.

EXAMPLE 1

In this example, *Irpex lacteus* No. 82 (NRRL 11063) (FERM-P No. 1009) is used as a seed strain and a medium comprising 40 g/l cane sugar, 30 g/l distillers soluble, 3 g/l powdered yeast extract, 1 g/l KH$_2$PO$_4$ and 0.2 g/l MgSO$_4$·7H$_2$O (pH 4.0 before sterilization) is used as a first medium. One loopful of the seed strain is inoculated into 30 ml of the first seed medium in 250 ml-Erlenmeyer flask and cultured with shaking at 30° C. for 4 days. Then, 30 ml of the thus prepared first seed culture is inoculated into 300 ml of a second seed medium in 2 l flask. The second seed medium has the same composition as that of the first seed medium. The second seed culturing is carried out with shaking at 30° C. for 2 days.

Then, 300 ml of the second seed culture is inoculated into 15 l of a main fermentation medium in a 30 l jar-fermenter. A medium comprising 20 g/l cellulose powder, 30 g/l soybean meal, 5 g/l Ebios (trade mark), 5 g/l KH$_2$PO$_4$ and 0.5 g/l MgSO$_4$·7H$_2$O (pH 4.0 before sterilization) is used as the main fermentation medium. Culturing in the jar fermenter is carried out with aeration and stirring (revolution: 400 r.p.m.: aeration: 15 l/min.) at 28° C. for three days.

After the completion of culturing, the cellulose activity of the culture filtrate obtained by filtering the microorganism cells is 600 μ/ml.

6.5 Kg of ammonium sulfate is added to 10 l of the filtrate to form a precipitate. The precipitate is dissolved in water and the resultant solution is subjected to using Sephadex G-25. 150 g of enzyme composition is obtained by freeze-drying. The enzyme activities of the enzyme composition are as follows.

| | | |
| --- | --- | --- |
| Cellulase | 23,000 | u/g |
| Xylanase | 2,800 | r/mg-hr |
| Laminarinase | 2,300 | r/mg-hr |
| Dextranase | 80 | r/mg-hr |
| Amylase | 14 | u/mg |
| Protease | 9 | u/mg |
| Pectinase | 53 | %/0.3 mg |

What is claimed is:

1. A method for increasing the amount of secretion of livestock milk which comprises daily administering to a livestock, a feedstuff containing an enzyme composition having activities of 20,000–40,000 (μ/g) cellulase, 2,000–4,600 (r/mg-hr) laminarinase, 1,600–3,400 (r/mg-hr) xylanase, 10–120 (r/mg-hr) dextranase, 28–81 (%/0.3 mg) pectinase, 4–15 (μ/mg) amylase and 2–20 (μ/mg) protease which is obtained by culturing Basidiomycetes belonging to the genus Irpex, in a ratio of one or more units of cellulase activity per gram of the dry matter of feedstuff.

2. The method according to claim 1, wherein said Basidiomycetes is selected from *Irpex lacteus* NRRL 11063 and *Irpex lacteus* ATCC 20123.

3. The method according to claim 1, wherein the amount of enzyme composition administered is from 2–6 units of the enzyme composition based on the cellulase activity per gram of the dry matter of feedstuff.

4. A method for increasing the amount of secretion of livestock milk which comprises daily administering to a livestock, a feedstuff containing an effective amount of an enzyme composition to effect an increase in the amount of secretion of milk of livestock as to that amount of secretion occurring without the administration of said enzyme composition, said enzyme composition having activities of 20,000–40,000 (μ/g) cellulase, 2,000–4,600 (r/mg-hr) laminarinase, 1,600–3,400 (r/mg-hr) xylanase, 10–120 (r/mg-hr) dextranase, 26–81 (%/0.3 mg) pectinase, 4–15 (μ/mg) amylase and 2–20 (μ/mg) protease which is obtained by culturing Basidiomycetes belonging to the genus Irpex.

5. The method according to claim 4, wherein said Basidiomycetes is selected from *Irpex lacteus* NRRL 11063 and *Irpex lacteus* ATCC 20123.

* * * * *